United States Patent [19]
McAnalley

[11] Patent Number: 5,961,957
[45] Date of Patent: Oct. 5, 1999

[54] FOAM COMPOSITIONS

[76] Inventor: Bill H. McAnalley, 4921 Corn Valley, Grand Prairie, Tex. 75052

[21] Appl. No.: 09/174,800

[22] Filed: Oct. 19, 1998

Related U.S. Application Data

[60] Provisional application No. 60/063,174, Oct. 20, 1997.

[51] Int. Cl.⁶ .......................... A61L 9/04; A61K 31/425
[52] U.S. Cl. .............................. 424/45; 514/372; 514/373
[58] Field of Search ................................ 424/45; 514/372, 514/373

[56] References Cited

U.S. PATENT DOCUMENTS 5,126,136  6/1992  Merat et al. ............................ 424/401
5,208,013  5/1993  Klein ...................................... 424/59

FOREIGN PATENT DOCUMENTS 2129618  12/1971  Germany .
8701844   3/1989  Netherlands .

Primary Examiner—Kevin E. Weddington
Attorney, Agent, or Firm—Randall C. Brown; Rick Matos; Akin, Gump, Strauss, Hauer & Feld, L.L.P.

[57] ABSTRACT

This invention pertains to the field of foam compositions for application to the skin of a user. More specifically, the invention relates to foam compositions that act as a barrier to water, allergens, poisons, toxins and other skin irritants when applied to the skin of a user.

2 Claims, No Drawings

FOAM COMPOSITIONS

CROSS-REFERENCE TO RELATED APPLICATION

This application claims the benefit of prior filed copending U.S. Provisional Application No. 60/063,174 filed Oct. 20, 1997.

FIELD OF THE INVENTION

The present invention pertains to the field of moisture and irritant barrier compositions for application to the skin of a user. More specifically, the invention relates to foam compositions that act as a barrier to moisture, allergens, poisons, toxins and other skin irritants when applied to the skin of a user.

DESCRIPTION OF THE PRIOR ART AND OTHER INFORMATION

There are many occupations and activities that require people to repeatedly place their hands in contact with or expose their hand to moisture or other skin irritants such as health care providers, flight attendants, beauticians, mechanics and restaurant employees. There are many other occupations and activities that require people to put their hands into contact with allergens and other irritants such as surgeons who must wear latex gloves when performing surgery and housewives who repeatedly wash their hands, wash dishes by hand or wear rubber gloves to wash dishes. Many such surgeons and housewives are allergic to latex gloves or rubber gloves and develop dermatitis or a rash as a result.

There are many other activities and occupations that involve exposing and contacting the skin with materials that are difficult to remove from the skin once they come into contact with the skin. For instance mechanics put their hands into contact with grease and motor oil on a daily basis and landscapers and gardeners put their hands into contact with soil and plants on a daily basis.

There are still other activities that would benefit from an effective skin protector or barrier composition. For instance, people who spend a significant amount of time outside are exposed to harmful radiation from the sun and need an effective sunscreen composition that is truly resistant to water. In addition, people who spend a significant amount of time outside often have a need for a water resistant insect repellent and a water resistant skin protector composition that isolates the skin from plant irritants such as from poison ivy, poison oak and poison sumac.

In view of these above-noted problem and needs, man skin protectors or barrier creams have been developed, however, these products have largely been ineffective. Some of such products have actually aggravated rather than ameliorated the effect of various irritants on the skin.

A need remains, therefore, for an effective skin protector or barrier that is resistant to water and a wide range of allergens, poisons, toxins and other skin irritants.

SUMMARY OF THE INVENTION

The present invention overcomes the disadvantages and drawbacks of the prior art.

It is an object of the present invention to provide an effective skin protector or barrier cream that is resistant to water and a wide range of skin allergens, poisons, toxins and other skin irritants.

It has now been demonstrated herein by the present inventor that a foam composition that includes deionized water, butane, glyceryl monostearate, dimethicone, propane, lanolin, stearic acid, methylchloroisothiazolinone/methylisothiazolinone provides an effective skin protector or barrier cream that is resistant to water and a wide range of allergens, poisons, toxins and skin irritants.

Accordingly, a first embodiment of the invention provides a foam composition that provides an effective barrier to water, allergens and other skin irritants. Preferably, the foam composition is dispensed onto a user's hands and massaged thoroughly into the skin in a manner similar to hand lotion. When the user has completed the activity in which the user's hands were exposed to the water, allergens or other skin irritants, the foam composition may be simply washed off with soap.

DETAILED DESCRIPTION

The foam compositions of the present invention provide an effective skin protector or barrier cream that is resistant to water and a wide range of skin allergens, poisons, toxins and other skin irritants. The foam compositions of the present invention preferably include deionized water, butane, glyceryl monostearate, dimethicone, propane, lanolin, stearic acid and methylchloroisothiazolinone/methylisothiazolinone. Preferably the foam compositions of the present invention are charged into an aerosol canister in conventional manner well known to those of ordinary skill in the art along with a propellant, which propellant preferably comprises butane and propane. The foam compositions of the present invention provide an effective skin protector or barrier cream that is resistant to water and a wide range of allergens, poisons, toxins and skin irritants. The foam compositions of the present invention are especially useful for health care providers, flight attendants, beauticians, mechanics, restaurant employees or anyone that is subject to skin conditions caused by constant exposure to moisture or other irritants.

According to a first embodiment, the foam compositions of the present invention provide an effective barrier to water, allergens, poisons, toxins and other skin irritants. The barrier foams of the present invention help prevent the following skin conditions: eczema, latex allergies, contact irritation, chemical absorption, dermatitis, chemical burns, soap irritations, dry skin conditions, dishpan hands, diaper rash and windburned skin.

The foam compositions of the present invention preferably are applied to clean and dry skin. When protecting hands, a walnut-sized amount is sufficient to provide an effective barrier. The foam is rubbed into the skin, covering all areas of the skin that are to be protected. Preferably, approximately three (3) minutes are allowed for absorption of the compositions into the skin before the skin is exposed to a skin irritant. Each application of the foam composition of the present invention provides an effective barrier for at least four (4) hours. After application of the foam composition of the present invention to the skin, the skin breathes and perspires normally. In addition, there is no change to the sense of touch and the barrier created by the foam is still effective even after repeated washing.

According to a preferred embodiment of the present invention, the foam compositions are prepared according to the following formula:

| Ingredients | % w/w |
|---|---|
| Deionized water | 70.00–90.00 |
| Butane | 7.00–9.00 |
| Glyceryl monostearate | 2.00–4.00 |
| Dimethicone copolyol | 1.50–3.50 |
| Propane | 1.00–3.00 |
| Lanolin | 0.50–2.50 |
| Stearic acid | 0.50–2.50 |
| Methylchloroisothiazolinone/methylisothiazolinone | 0.05–1.05 |

According to a further preferred embodiment of the present invention, the foam compositions are prepared according to the following formula:

| Ingredients | % w/w |
|---|---|
| Deionized water | 82.38 |
| Butane | 8.00 |
| Glyceryl monostearate | 2.88 |
| Dimethicone copolyol | 2.52 |
| Propane | 2.00 |
| Lanolin | 1.26 |
| Stearic acid | 0.90 |
| Methylchloroisothiazolinone/methylisothiazolinone | 0.06 |

The above is a detailed description of particular embodiments of the invention. The components of the above-noted compositions of the present invention are commercially available from sources such as Aldrich Chemical Company, Milwaukee, Wis. Those of ordinary skill in the art should, in light of the present disclosure, appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

As used herein and unless otherwise indicated, the terms "a" and "an" are taken to mean "one", "at least one" or "one or more".

What is claimed is:

1. A barrier foam composition comprising:

from 70.00 to 90.00 percent by weight of water, from 7.00 to 9.00 percent by weight of butane, from 2.00 to 4.00 percent by weight of glyceryl monostearate, from 1.50 to 3.50 percent by weight of dimethicone copolyol, from 1.00 to 3.00 percent by weight of propane, from 0.50 to 2.50 percent by weight of lanolin, from 0.50 to 2.50 percent by weight of stearic acid and from 0.05 to 1.05 percent by weight of at least one of methylchloroisothiazolinone and methylisothiazolinone;

whereby said composition protects the skin of a user from water, allergens or other skin irritants.

2. A barrier foam composition according to claim 1, comprising:

about 82.38 percent by weight of water, about 8.00 percent by weight of butane, about 2.88 percent by weight of glyceryl monostearate, about 2.52 percent by weight of dimethicone copolyol, about 2.00 percent by weight of propane, about 1.26 percent by weight of lanolin, about 0.90 percent by weight of stearic acid and about 0.06 percent by weight of at least one of methylchloroisothiazolinone and methylisothiazolinone.

* * * * *